US007682636B2

(12) United States Patent
Babish et al.

(10) Patent No.: US 7,682,636 B2
(45) Date of Patent: *Mar. 23, 2010

(54) CURCUMINOID COMPOSITIONS EXHIBITING SYNERGISTIC INHIBITION OF THE EXPRESSION AND/OR ACTIVITY OF CYCLOOXYGENASE-2

(75) Inventors: John G. Babish, Brooktondale, NY (US); Terrence M. Howell, Lansing, NY (US); Linda M. Pacioretty, Brooktondale, NY (US)

(73) Assignee: Metaproteomics, LLC, San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/701,583

(22) Filed: Feb. 2, 2007

(65) Prior Publication Data
US 2007/0141183 A1 Jun. 21, 2007

Related U.S. Application Data

(60) Division of application No. 10/988,393, filed on Nov. 13, 2004, now Pat. No. 7,279,185, which is a continuation of application No. 10/282,236, filed on Oct. 25, 2002, now abandoned.

(60) Provisional application No. 60/335,062, filed on Oct. 26, 2001.

(51) Int. Cl.
*A01N 65/00* (2006.01)
(52) U.S. Cl. .................................................. 424/725
(58) Field of Classification Search ....................... None
See application file for complete search history.

(56) References Cited
U.S. PATENT DOCUMENTS

| 3,552,975 | A | | 1/1971 | Worden |
| 3,720,517 | A | | 3/1973 | Bavisotto et al. |
| 3,932,603 | A | | 1/1976 | Haas |
| 3,933,919 | A | | 1/1976 | Wilkinson |
| 3,965,188 | A | | 6/1976 | Westermann et al. |
| 4,123,561 | A | | 10/1978 | Grant |
| 4,133,903 | A | | 1/1979 | Thiele et al. |
| 4,154,865 | A | | 5/1979 | Grant |
| 4,401,684 | A | | 8/1983 | Versluys |
| 4,554,170 | A | | 11/1985 | Panzer et al. |
| 4,644,084 | A | | 2/1987 | Cowles et al. |
| 4,692,280 | A | | 9/1987 | Spinelli |
| 4,767,640 | A | | 8/1988 | Goldstein et al. |
| 5,006,337 | A | | 4/1991 | Motitschke et al. |
| 5,013,571 | A | | 5/1991 | Hay |
| 5,073,396 | A | | 12/1991 | Todd, Jr. |
| 5,082,975 | A | * | 1/1992 | Todd et al. ............... 568/315 |
| 5,155,276 | A | | 10/1992 | Paul |
| 5,166,449 | A | | 11/1992 | Todd, Jr. et al. |
| 5,264,236 | A | | 11/1993 | Ogasahara et al. |
| 5,286,506 | A | | 2/1994 | Millis et al. |
| 5,387,425 | A | | 2/1995 | Hsu et al. |
| 5,604,263 | A | | 2/1997 | Tobe et al. |
| 5,827,895 | A | | 10/1998 | Nutter et al. |
| 5,296,637 | A | | 2/2000 | Ting et al. |
| 6,020,019 | A | | 2/2000 | Ting et al. |
| 6,129,907 | A | | 10/2000 | Sreenivasan et al. |
| 6,200,594 | B1 | | 3/2001 | Ernest et al. |
| 6,383,527 | B1 | | 5/2002 | Artman et al. |
| 6,391,346 | B1 | | 5/2002 | Newmark et al. |
| 6,583,322 | B1 | | 6/2003 | Shalai et al. |
| 2002/0086062 | A1 | | 7/2002 | Kuhrts |
| 2002/0086070 | A1 | | 7/2002 | Kuhrts |
| 2003/0035851 | A1 | | 2/2003 | Chen |
| 2004/0072900 | A1 | | 4/2004 | Artman et al. |

FOREIGN PATENT DOCUMENTS

| DE | 2212148 | 9/1973 |
| JP | 363211219 | 9/1988 |
| JP | 08073369 | 3/1996 |
| JP | 410025247 | 1/1998 |
| WO | 0068356 | 11/2000 |
| WO | 0202582 | 1/2002 |
| WO | WO 2003/035007 | 5/2003 |
| WO | WO 2005/084230 | 9/2005 |
| WO | WO 2006/053249 | 5/2006 |

OTHER PUBLICATIONS

Supplementary European Search Report from corresponding EP Application No. 05851567, 8pp.
European Search Report for related European Application No. 02784313.5.
Abstract of Database WPI Week, 1996, Derwent Publications Ltd., London.
Anto, et al., "Anti-inflammatory Activity of Natural and Synthetic Curcuminoids", Pharmacy and Pharmacology Communications, vol. 4, No. 2, 1998, 103-106.
Chandra, et al., "Anti-inflammatory and Anti-Arthritic Activity of Volatile Oil of *Curcuma longa* (Haldi)", Indian Journal of Med. Research, vol. 60, No. 1, 1972, 138-142.
Bermejo, et al. Rev. Esp. Enferm. Dig. 95: 621-624 and 625-628 (2003).

(Continued)

*Primary Examiner*—Michael V Meller
(74) *Attorney, Agent, or Firm*—McDermott Will & Emery LLP

(57) ABSTRACT

A novel formulation is provided that serves to inhibit the inflammatory response in animals. The formulation comprises, as a first component an effective amount of a curcuminoid species and an effective amount of a second component selected from the group consisting of an alpha-acid species or a beta-acid species or derivatives thereof. The composition provides synergistic anti-inflammatory effects in response to physical or chemical injury or abnormal immune stimulation due to a biological agent or unknown etiology.

6 Claims, 3 Drawing Sheets

OTHER PUBLICATIONS

Brown, et al. J. Chem. Soc. 545 (1959).
Byrne, et al. J. Chem. Soc. (C):2810 (1971).
Carroccio, et al. Clin. Chem. 49:861-867 (2003).
Carson, J. Am. Chem. Soc. 73:1850-1851 (1951).
Charlier, et al. Eur. J. Med. Chem. 38:645-659 (2003).
Chou, et al. Adv Enzyme Regul 22:27-55 (1984).
Chou, et al. Eur. J. Biochem. 115:207-216 (1981).
Chou, et al. J. Biol. Chem. 252:6438-6442 (1977).
Chou, et al. J. Theor. Biol. 35:285-297 (1972).
Chou, J. Theor. Biol. 59:253-276 (1976).
Chou, et al. TIPS, vol. 4, 450-454 (1983).
Costa, et al. Digest. Liver Dis. 35:642-647 (2003).
Ding, et al. Biochem. Biophy. Res. Comm. 261:218-223 (1999).
Goldstein, et al. Am. J. Gastroenterol. 96:1019-1027 (2001).
Halter, et al. Gut 49:443-453 (2001).
Hammberg, et al. J. Bio. Chem. 246:6713-6721 (1971).
Kanematsu, et al. J Bone Miner Res 12(11):1789-1796 (1997).
Lopes, Curr. Med Res Opin. 8:145-149 (1982).
Meling, et al. Scand. J. Gastroenterol. 31:339-344 (1996).
Noreen, et al. J. Nat. Prod 61:2-7 (1998).
Pairet, et al. Inflamm. Res 47, Supplement 2S93-S101 (1998).
Panglisch, Monafsschrift fuer Brauwissen Schaft, 1990, 43(1), 4-16.
Ringbom, et al. J. Nat Prod 61:1212-1215 (1998).
Pippa, et al. Scand. J. Gastroenterol. Suppl. 167:32-35 (1989).
Poullis, et al. J. Gastroenterol. Hepatol. 18:756-762 (2003).
Røseth, Digest. Liver Dis. 35:607-609 (2003).
Shah, et al. Gut 48:339-346 (2001).
Schjerven, et al. Br. J. Dermatol. 149:484-491 (2003).
Shureiqi, et al. Cancer Res. 61:6307-6312 (2001).
Sivri, Fundam. Clinic. Pharmacol. 18:23-31 (2004).
Subbaramaiah, et al. Cancer Res. 60:2399-2404 (2000).
Suh, et al. Cancer Res 58:717-723 (1988).
Newark, et al., "Beyond Aspirin", pp. 147-150, Hohm Press (2000).
Tagashira, et al., Biosci, Biotech. Biochem. 59(4):740-742 (1996).
Tibble, et al. Drugs Today 37:85-96 (2001).
Tibble, et al. Gut 45:362-366 (1999).
Tobe, et al. Biosci. Biotech. Biochem 61(1):158-159 (1997).
Wang, et al. Free Radical Biology & Medicine 27:612-616 (1999).
Warner, et al. Proc Natl Acad Sci USA 96:7563-7568 (1999).
Yamamoto, FEBS Letters 465:103-106 (2000).
Yui, et al. Biol. Pharm. Bull. 26:753-760 (2003).
Information on "Zyflamend and Zyflamend PM", downloaded from Internet Aug. 30, 2002.
Information on ArthroTrimTM product, downloaded from Internet Aug. 30, 2002.
Germany, "The Absolutely German Drink," contents of beer, 2004, 5 pages.
Information on "Hops and Beer Flavours", IOB Technical Symposium, Apr. 2001, pp. 1-9.
Verzele, et al. Chemistry and analysis of hop and beer bitter acids, Developments in food science, 27, pp. 44-51, 88-139.

* cited by examiner

[A]

[B]

[C]

[D]

[E]

[F]

[A]

[B]

or

[A]

[B]

CURCUMINOID COMPOSITIONS EXHIBITING SYNERGISTIC INHIBITION OF THE EXPRESSION AND/OR ACTIVITY OF CYCLOOXYGENASE-2

CROSS-REFERENCE TO RELATED APPLICATIONS

This application is a divisional of U.S. application Ser. No. 10/988,393, filed on Nov. 13, 2004, now U.S. Pat. No. 7,279,185, which is a continuation of U.S. application Ser. No. 10/282,236, filed on Oct. 25, 2002, now abandoned, which claims the benefit under 35 U.S.C. §119(e) to U.S. provisional application No. 60/335,062, filed Oct. 26, 2001. The contents of each of the earlier applications are hereby incorporated by reference as if recited herein in their entirety.

BACKGROUND OF THE INVENTION

1. Field of the Invention

The present invention relates generally to a composition exhibiting synergistic inhibition of the expression and/or activity of inducible cyclooxygenase-2 (COX-2). The composition can function synergistically to inhibit the inducibility and/or activity of inducible cyclooxygenase (COX-2) with little or no significant effect on constitutive cyclooxygenase (COX-1).

2. Description of the Related Art

Inflammatory diseases affect more than fifty million Americans. As a result of basic research in molecular and cellular immunology over the last ten to fifteen years, approaches to diagnosing, treating and preventing these immunologically-based diseases has been dramatically altered. One example of this is the discovery of an inducible form of the cyclooxygenase enzyme. Constitutive cyclooxygenase (COX), first purified in 1976 and cloned in 1988, functions in the synthesis of prostaglandins (PGs) from arachidonic acid (AA). Three years after its purification, an inducible enzyme with COX activity was identified and given the name COX-2, while constitutive COX was termed COX-1.

COX-2 gene expression is under the control of pro-inflammatory cytokines and growth factors. Thus, the inference is that COX-2 functions in both inflammation and control of cell growth. While COX-2 is inducible in many tissues, it is present constitutively in the brain and spinal cord, where it may function in nerve transmission for pain and fever. The two isoforms of COX are nearly identical in structure but have important differences in substrate and inhibitor selectivity and in their intracellular locations. Protective PGs, which preserve the integrity of the stomach lining and maintain normal renal function in a compromised kidney, are synthesized by COX-1. On the other hand, PGs synthesized by COX-2 in immune cells are central to the inflammatory process.

An ideal formulation for the treatment of inflammation would inhibit the induction and activity of COX-2 without affecting the activity of COX-1. However, conventional non-steroidal and steroidal anti-inflammatory drugs lack the specificity of inhibiting COX-2 without affecting COX-1 and are at risk to cause damages on the gastrointestinal system when used for extended periods.

Numerous studies have shown that the relative incidence of gastrointestinal (GI) side effects can be correlated to the relative COX-2 specificity of the agents. The higher the specificity for COX-2 over COX-1, the lower the incidence of GI upset. Thus, aspirin, with a COX-2 specificity of only 0.6, produces a greater incidence of GI distress than curcuminoids, with a reported COX-2 specificity of nearly 3.0. However, the generally accepted COX-2 specificity necessary to significantly reduce the probability of GI upset is 5.0.

Therefore, it would be useful to identify a composition that would specifically inhibit or prevent the expression of COX-2 enzymatic activity, while having little or no effect on COX-1 metabolism so that these could be used at sufficiently low doses or at current clinical doses, with no adverse side effects.

Medical doctors generally utilize non-steroidal and steroidal anti-inflammatory drugs for treatment of osteoarthritis. These drugs, however, are not well adapted for long-term therapy because they not only lack the ability to promote and protect cartilage; they can actually lead to degeneration of cartilage or reduction of its synthesis. Moreover, most non-steroidal, anti-inflammatory drugs damage the gastrointestinal system when used for extended periods. Thus, new treatments for arthritis are urgently needed.

The joint-protective properties of glucosamine would make it an attractive therapeutic agent for osteoarthritis except for two drawbacks: (i) the rate of response to glucosamine treatment is slower than for treatment with anti-inflammatory drugs, and (ii) glucosamine may fail to fulfill the expectation of degenerative remission. In studies comparing glucosamine with non-steroidal anti inflammatory agents, for example, a double-blinded study comparing 1500 mg glucosamine sulfate per day with 1200 mg ibuprofen, demonstrated that pain scores decreased faster during the first two weeks in the ibuprofen patients than in the glucosamine-treated patients. However, the reduction in pain scores continued throughout the trial period in patients receiving glucosamine and the difference between the two groups turned significantly in favor of glucosamine by week eight. Lopes Vaz, A., *Double-blind clinical evaluation of the relative efficacy of ibuprofen and glucosamine sulphate in the management of osteoarthritis of the knee in outpatients,* 8 Curr. Med Res Opin. 145-149 (1982). Thus, glucosamine may relieve the pain and inflammation of arthritis, but at a slower rate than the available anti-inflammatory drugs.

Moreover, the currently available glucosamine formulations have not been formulated to optimally attack and alleviate the underlying causes of osteoarthritis and rheumatoid arthritis. Also, as with many commercially-available herbal and dietary supplements, the available formulations do not have a history of usage, nor controlled clinical testing, which might ensure their safety and efficacy.

An ideal formulation for the normalization of cartilage metabolism or treatment of osteoarthritis would provide adequate chondroprotection with potent antiinflammatory activity. The optimal dietary supplement for osteoarthritis should enhance the general joint rebuilding qualities offered by glucosamine and attenuate the inflammatory response without introducing any harmful side effects. It should be inexpensively manufactured and comply with all governmental regulations.

SUMMARY OF THE INVENTION

Thus, it would be useful to identify a natural formulation of compounds that would specifically inhibit or prevent the synthesis of prostaglandins by COX-2 with little or no effect on COX-1. Such a formulation, which would be useful for preserving the health of joint tissues, for treating arthritis or other inflammatory conditions, has not previously been discovered. The term "specific or selective COX-2 inhibitor" embraces compounds or mixtures of compounds that selectively inhibit COX-2 over COX-1. Preferably, the compounds have a median effective concentration for COX-2 inhibition that is minimally five times greater than the median effective concentration for the inhibition of COX-1. For example, if the median inhibitory concentration for COX-2 of a test formulation was 0.2 μg/mL, the formulation would not be considered COX-2 specific unless the median inhibitory concentration for COX-1 was equal to or greater than 1 μg/mL.

The preferred embodiments provide a composition comprising, as a first component, a curcuminoid species and a second compound that can synergistically enhance the anti-inflammatory effect of the curcuminoid. The composition comprises an effective amount of a first component comprising a curcuminoid species and a second component comprising a member selected from the group consisting of an alpha acid, a beta acid, and derivatives thereof. In a certain embodiment, the alpha acid is humulone. In another embodiment, the beta acid is lupulone. In another embodiment, the curcuminoid is curcumin.

In a certain embodiment, the composition further comprises a member selected from the group consisting of glucosamine and chondrotin sulfate.

The preferred embodiments also provide a method of treating inflammation or inflammation-based diseases in an animal which comprises providing to the animal suffering symptoms of inflammation a composition comprising an effective amount of a first component comprising a curcuminoid species and a second component comprising a member selected from the group consisting of an alpha acid, a beta acid, and derivatives thereof.

The preferred embodiments also provide a method of reducing the symptoms of osteoarthritis in an animal which comprises providing to the animal suffering symptoms of inflammation a composition comprising an effective amount of a first component comprising a curcuminoid species and a second component comprising a member selected from the group consisting of an alpha acid, a beta acid, and derivatives thereof.

DETAILED DESCRIPTION OF THE PREFERRED EMBODIMENT

Figure 1:
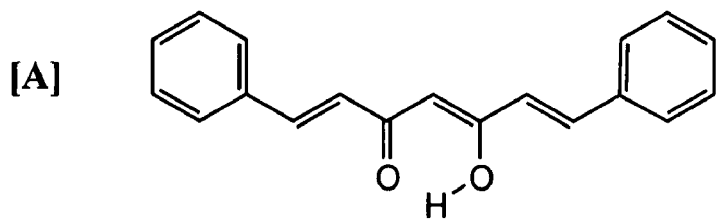
FIGS. 1[A]-[F] illustrate the general chemical structure of [A] the curcuminoid genus and [B], [C], [D], [E] and [F], respectively, as curcumin, demethoxycurcumin, bis-demethoxycurcumin, the cis-trans geometrical isomer of curcumin, and cyclocurcumin as species within that genus.
Figure 1:
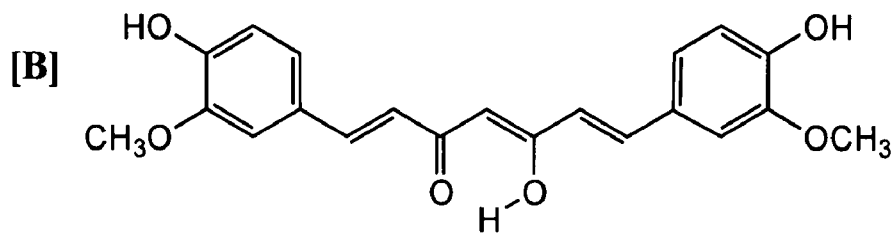
Figure 1:
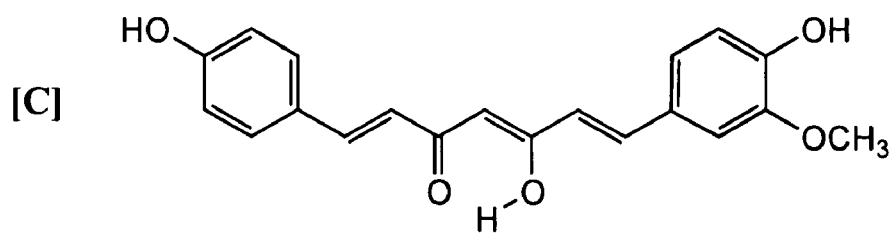
Figure 1:
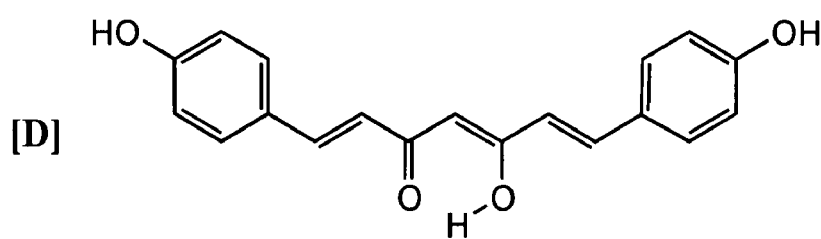
Figure 1:
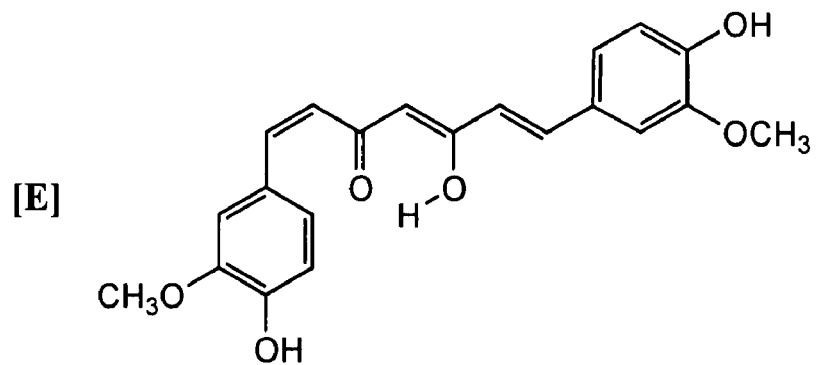
Figure 1:
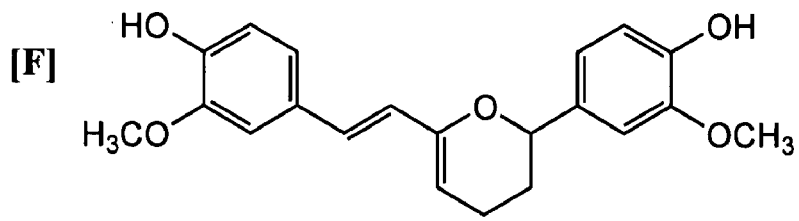

It must be noted that, as used in this specification and the appended claims, the singular forms "a," "an," and "the" include plural referents unless the context clearly dictates otherwise.

The preferred embodiments provide compositions having a synergistic inhibitory effect on the expression and/or activity of COX-2. More particularly, the composition comprises, as a first component, a curcuminoid and, as a second component, a member selected from the group consisting of an alpha-acid, a beta-acid, and derivatives thereof, as more specifically described below. The composition provided by the preferred embodiments can be formulated as a dietary supplement or therapeutic composition. The composition can function synergistically to inhibit the inducibility and/or activity of COX-2 with no significant effect on COX-1.

As used herein, the term "dietary supplement" refers to compositions consumed to affect structural or functional changes in physiology. The term "therapeutic composition" refers to any compounds administered to treat or prevent a disease.

As used herein, the terms "curcuminoid" and "active curcuminoid" refer to species within the curcuminoid genera that is capable of inhibiting the inducibility and/or activity of COX-2 while having little or no effect on COX-1 or is capable of inhibiting or reducing the severity of an inflammatory response. The curcuminoid can be extracted from natural products or chemically synthesized.

A yellow pigmented fraction isolated from the rhizomes of *Curcuma longa* contains curcuminoids belonging to the dicinnamoyl methane group. Curcuminoids are present to the extent of 3 to 5 percent. They are considered the most important active ingredients and are believed to be responsible for the biological activity of *Curcuma longa*. Though their major activity is anti-inflammatory, curcuminoids have been reported to possess antioxidant, anti-allergic, wound healing, antispasmodic, antibacterial, antifungal and antitumor activity as well. Curcumin (FIG. 1B) was isolated in 1815 and structurally defined in 1910. Other curcuminoids isolated from *Curcum longa* include demethoxycurcumin (FIG. 1C), bisdemethoxycurcumin (FIG. 1D), a cis-trans geometrical isomer of curcumin (FIG. 1E), and cyclocurcumin (FIG. 1F). Curcuminoids may be found in other botanicals in addition to *Curcuma longa*, such as *Curcuma xanthorrhiza* and *Curcuma zedoaria*.

Curcuminoids are well known for their anti-inflammatory activity. Tumeric is one of the oldest anti-inflammatory drugs used in Ayurvedic medicine. The anti-inflammatory activity of curcuminoids has been evaluated in inflammatory reaction models such as chemical or physical irritants like carrageenin, cotton pellets, formaldehyde and the granuloma pouch. Human, double-blinded, clinical trials have demonstrated efficacy in rheumatoid arthritis at a dose of 1200 mg curcuminoids/day for five to six weeks. At these doses, however, signs of gastrointestinal (GI) discomfort and stomach irritation are frequently reported. The GI upset and stomach irritation caused by high doses of curcuminoids may be due to the fact that curcuminoids act on prostaglandin production in a manner similar to that of aspirin and aspirin-like anti-inflammatory agents.

Preferably, the curcuminoid genus, as represented by FIG. 1[A], and specifically exemplified by curcumin in FIG. 1[B] is a pharmaceutical grade botanical extract such as can be obtained commercially, for example, from Sabinsa (121 Ethel Road West, Piscataway, N.J.). Other curcuminoids that may be employed include demethoxycurcumin (FIG. 1[C]), bis-demethoxycurcumin (FIG. 1[D]), a cis-trans curcumin (FIG. 1E), and cyclocurcumin (FIG. 1F). The curcuminoid used can be readily obtained from *Curcuma longa* L. Pharmaceutical grade curcuminoid extract is standardized to have a curcuminoid content of greater than about 70 percent. The pharmaceutical, botanical grade extract preferably should have passed extensive safety and efficacy procedures. As employed in the preferred embodiments, the extract has a curcuminoid content of about 1 to 99 percent by weight. Preferably, the minimum curcuminoid content is about 70 percent by weight. Alternatively, the curcuminoid may be synthesized using standard techniques known in chemical synthesis.

As used herein, the term "hop extract" refers to the solid material resulting from (1) exposing a hops plant product to a solvent, (2) separating the solvent from the hops plant product, and (3) eliminating the solvent.

As used herein, the term "solvent" refers to a liquid of aqueous or organic nature possessing the necessary characteristics to extract solid material from the hop plant product. Examples of solvents would include, but are not limited to, water, steam, superheated water, methanol, ethanol, hexane, chloroform, liquid $CO_2$, liquid $N_2$ or any combinations of such materials.

As used herein, the term "$CO_2$ extract" refers to the solid material resulting from exposing a hops plant product to a liquid or supercritical $CO_2$ preparation followed by the removal of the $CO_2$.

As used herein, the term "alpha-acids" refers to compounds isolated from hops plant products including, but not limited to, humulone, cohumulone, isohumulone, isoprehumulone, hulupone, adhumulone, xanthohumol A and xanthohumol B.

As used herein, the term "beta-acids" refers to compounds collectively known as lupulones including, but not limited to, lupulone, colupulone, adlupulone, tetrahydroisohumulone, and hexahydrocolupulone.

As used herein, the term "essential oil fraction" refers to a complex mixture of components comprising myrcene, humulene, beta-caryophyleen, undecane-2-on, and 2-methyl-but-3-en-ol.

As used herein, the term "fats" refers to triacylglyerol esters of fatty acids.

As used herein, the term "waxes" refers to triacylglycerol ethers or esters of extremely long chain (>25 carbons) fatty alcohols or acids.

Hop extraction in one form or another goes back over 150 years to the early nineteenth century when extraction in water and ethanol was first attempted. Even today an ethanol extract is available in Europe, but by far the predominant extracts are organic solvent extracts (hexane) and $CO_2$ extracts (supercritical and liquid). $CO_2$ (typically at 60 bars pressure and 5 to 10° C.) is in a liquid state and is a relatively mild, non-polar solvent highly specific for hop soft resins and oils. Beyond the critical point, typically at 300 bars pressure and 60° C., $CO_2$ has the properties of both a gas and a liquid and is a much stronger solvent. The approximate components of the various extracts is compared in Table 1.

TABLE 1

Hop Extracts (Percent W/W)

| Component | Hops | Organic Solvent Extract | Super-Critical $CO_2$ | Liquid $CO_2$ |
|---|---|---|---|---|
| Total resins | 12-20 | 15-60 | 75-90 | 70-95 |
| Alpha-acids | 2-12 | 8-45 | 27-55 | 30-60 |
| Beta-acids | 2-10 | 8-20 | 23-33 | 15-45 |
| Essential oils | 0.5-1.5 | 0-5 | 1-5 | 2-10 |
| Hard resins | 2-4 | 2-10 | 5-11 | None |
| Tannins | 4-10 | 0.5-5 | 0.1-5 | None |
| Waxes | 1-5 | 1-20 | 4-13 | 0-10 |
| Water | 8-12 | 1-15 | 1-7 | 1-5 |

At its simplest, hop extraction involves milling, pelleting and re-milling the hops to spread the lupulin, passing a solvent through a packed column to collect the resin components and finally, removal of the solvent to yield a whole or "pure" resin extract.

The main organic extractants are strong solvents and in addition to virtually all the lupulin components, they extract plant pigments, cuticular waxes, water and water-soluble materials.

Supercritical $CO_2$ is more selective than the organic solvents and extracts less of the tannins and waxes and less water and hence water-soluble components. It does extract some of the plant pigments like chlorophyll but less than the organic solvents do. Liquid $CO_2$ is the most selective solvent used commercially for hops and hence produces the most pure whole resin and oil extract. It extracts none of the hard resins or tannins, much lower levels of plant waxes, no plant pigments and less water and water-soluble materials.

As a consequence of this selectivity and the milder solvent properties, the absolute yield of liquid $CO_2$ extract per unit weight of hops is less than when using the other mentioned solvents. Additionally, the yield of alpha acids with liquid $CO_2$ (about 89-93%) is lower than that of supercritical $CO_2$ (about 91-94%) or the organic solvents (about 93-96%). Following extraction there is the process of solvent removal, which for organic solvents involves heating to cause volatilization. Despite this, trace amounts of solvent do remain in the extract. The removal of $CO_2$, however, simply involves a release of pressure to volatilize the $CO_2$.

In the preferred embodiments, the alpha acid, beta acid, or derivative thereof can be extracted from hops or chemically synthesized. Preferably, the alpha acid, beta acid, or derivative thereof is extracted from hops, more preferably extracted by supercritical $CO_2$.

Figure 2:
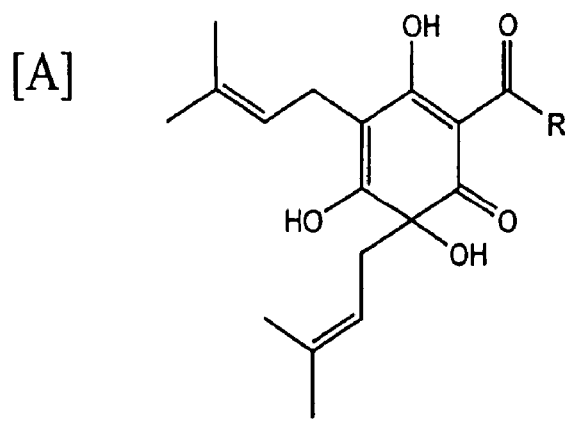
FIGS. 2[A] and [B], respectively, illustrate the general chemical structures of the alpha-acid genus and humulone as a species within that genus.
Figure 2:
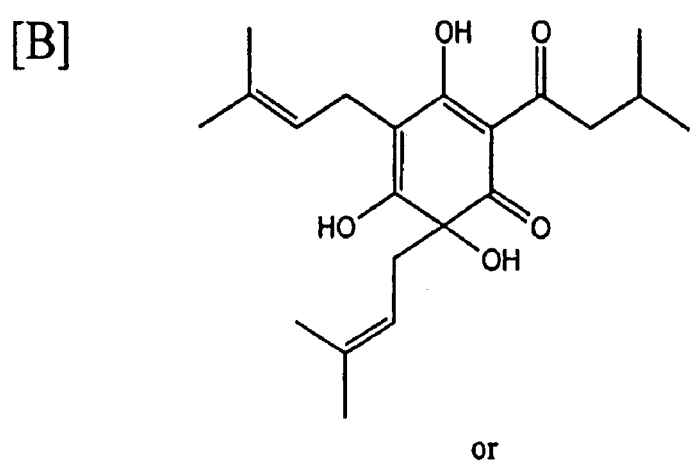
Figure 2:
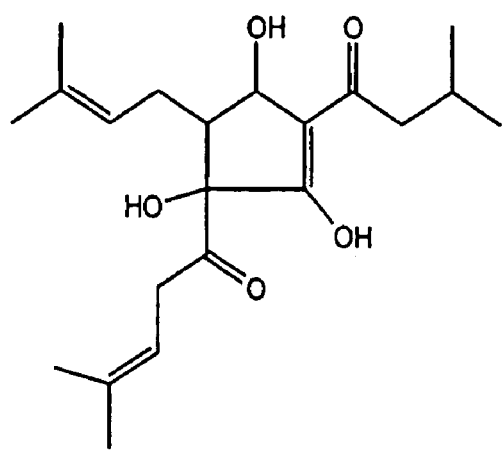
Figure 3:
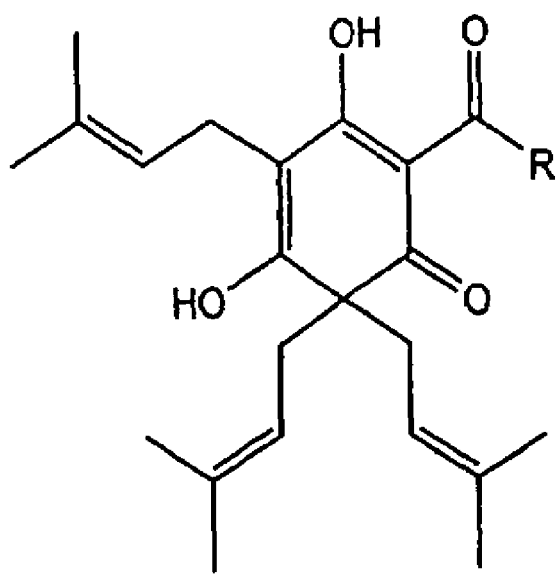
FIGS. 3[A] and [B], respectively, illustrate the general chemical structures of the beta-acid genus and lupulone
Figure 3:
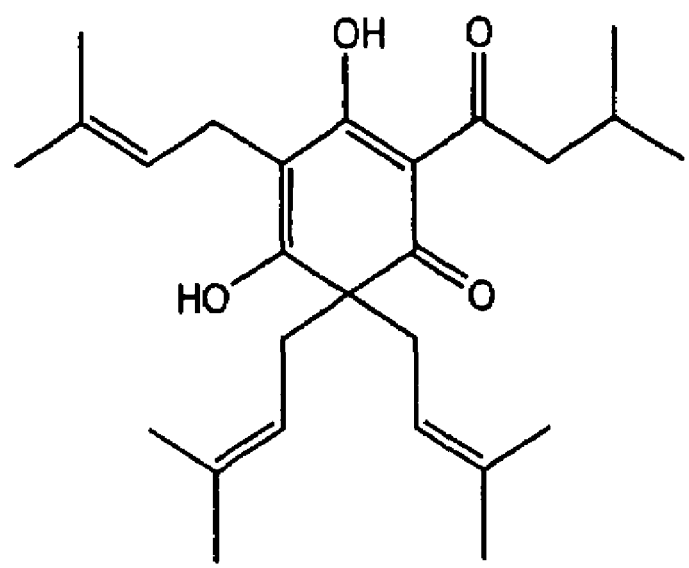

Preferably, the alpha-acid genus, as represented by FIG. 2 [A] and specifically exemplified by humulone in FIG. 2 [B], and the beta-acid genus, as represented by FIG. 3 [A] and specifically exemplified by lupulone (FIG. 3 [B]) is a pharmaceutical grade preparation such as can be obtained commercially, for example, from Hopunion. (Yakima, Wash.).

The identification of humulone from hops extract as an inhibitor of bone resorption is reported in Tobe, H. et al. 1997. [Bone resorption Inhibitors from hop extract. Biosci. Biotech. Biochem 61(1)158-159.] Later studies by the same group characterized the mechanism of action of humulone as inhibition of COX-2 gene transcription following TNFalpha stimulation of MC3T3 –E1 cells [Yamamoto, K. 2000. Suppression of cyclooxygenase-2 gene transcription by humulon of bee hop extract studied with reference to glucocorticoid. FEBS Letters 465:103-106]. However, these references disclose the use of humulone alone for the applications of osteoporosis and COX-2 gene transcription.

The preferred embodiments provide for modifying the curcuminoid molecule to achieve greater efficacy and lower toxicity and adding a second component that acts in a synergistic manner. Therefore, preferred embodiments relate to a discovery that when combining a curcuminoid with a second molecule selected from the group consisting of a alpha-acid, a beta-acid, and derivatives thereof, the combination produces a synergistic effect in a target cell. One such synergistic response would be the specific inhibition of inducible COX-2.

Representative species within each genus are listed in Table 2. Of the species listed under each genus in Table 2, those containing at least one asterisk (*) are preferred and those containing two asterisks (**) are particularly preferred.

TABLE 2

Components of Composition

| CURCUMINOIDS | ALPHA-ACIDS | BETA ACIDS |
|---|---|---|
| Curcumin** | Humulone** | Lupulone** |
| Demeth-oxycurcumin** | Cohumulone* | Colupulone* |

TABLE 2-continued

Components of Composition

| CURCUMINOIDS | ALPHA-ACIDS | BETA ACIDS |
|---|---|---|
| Bisdemeth-oxycurcumin** | Isohumulone* | Adlupulone* |
| Cis-trans curcumin* | Isoprehumulone* | Tetrahydroisohumulone* |
| Cyclocurcumin* | Hulupone* | Hexahydrocolupulone* |
| | Adhumulone* | Dihydro-isohumulone* |
| | Xanthohumulone A* | |
| | Xanthohumulone B* | |

Preferably, the preferred embodiments utilize active curcuminoid and active ingredients of hop extract or derivatives thereof. As used herein, the term "active curcuminoid", "active ingredient of hop extract" or derivatives thereof refers to naturally occurring or synthetic derivatives of species within the scope of the respective genera that are capable of inhibiting the inducibility and/or activity of COX-2 while having little or no effect on COX-1 or are capable of inhibiting or reducing the severity of an inflammatory response.

The preferred embodiments can also use conjugates of curcuminoids, alpha- and beta-acids or derivatives thereof. "Conjugates" of curcuminoids, alpha- and beta-acids or derivatives thereof means curcuminoids, alpha-acids, and beta-acids covalently bound or conjugated to a member selected from the group consisting of mono- or di-saccharides, amino acids, sulfates, succinate, acetate and glutathione. Preferably, the mono- or di-saccharide is a member selected from the group consisting of glucose, mannose, ribose, galactose, rhamnose, arabinose, maltose, and fructose.

A certain embodiment is a composition comprising an effective amount of curcumin and at least one compound selected from the group consisting of humulone and lupulone.

The inhibition of the activity of the COX-2 enzyme by alpha-acids or beta-acids can provide a dual, synergistic effect with curcuminoids. Thus, the second compound selected from the group consisting of alpha-acids and beta-acids can increase the anti-inflammatory activity of the curcuminoids. The result of the compositions of the preferred embodiments is a more selective effect on the activity of COX-2 at lower doses of curcuminoids than would normally be required. By decreasing the dose of curcuminoids to achieve the desired COX-2 inhibition, the probability of side effects from this compound decreases almost exponentially. The second compound selected from the group consisting of alpha-acids and beta-acids can provide benefits, such as, but not limited to, hepatoprotection, antitumor promotion, antihyperlipidermia, antihyperglycermia and protection against ulcer formation from COX-1 inhibition by the curcuminoids.

Preferably, a daily dose (mg/kg-day) of the preferred dietary supplement would be formulated to deliver, per kg body weight of the animal, about 0.001 to about 30.0 mg curcuminoids, and about 0.5 to about 20.0 mg alpha-acids or beta-acids.

The composition of the preferred embodiments for topical application would contain one of the following: about 0.001 to about 1 wt %, preferably about 0.01 to about 1 wt % curcuminoids, and about 0.025 to about 1 wt %, preferably about 0.05 to about 1 wt % alpha-acids or beta-acids.

The composition of the preferred embodiments would produce serum concentrations in the following range: about 0.0001 to about 10 μM of curcuminoids, and about 0.001 to about 10 μM alpha-acids or beta-acids.

In the preferred embodiments, the composition can further comprise glucosamine or chondroitin sulfate. Glucosamine is generally accepted as being effective and safe for treating osteoarthritis. Therefore, the compositions that further comprise glucosamine or chondroitin sulfate can aid in normalizing joint function or reducing the symptoms of osteoarthritis.

In addition to the combination of curcuminoids and alpha-acids, beta-acids or derivatives, the present composition for dietary application can include various additives such as, but not limited to, other natural components of intermediary metabolism, antioxidants, vitamins, minerals, proteins, fats, carbohydrates, and aminosugars, as well as inert ingredients such as, but not limited to, talc and magnesium stearate, that are standard excipients in the manufacture of tablets and capsules.

The composition of the preferred embodiments can further comprise a pharmaceutically acceptable carrier. As used herein, "pharmaceutically acceptable carrier" includes any and all solvents, dispersion media, coatings, isotonic and absorption delaying agents, sweeteners and the like. These pharmaceutically acceptable carriers can be prepared from a wide range of materials including, but not limited to, diluents, binders and adhesives, lubricants, disintegrants, coloring agents, bulking agents, flavoring agents, sweetening agents and miscellaneous materials such as buffers and absorbents that may be needed in order to prepare a particular therapeutic composition. The use of such media and agents for pharmaceutically active substances is well known in the art. Except insofar as any conventional media or agent is incompatible with the active ingredients, its use in the preferred embodiments is contemplated. In one embodiment, talc and magnesium stearate are included in the formulation. Preferable components are Astac Brand 400 USP talc powder and the veritable grade of magnesium stearate. Other ingredients known to affect the manufacture of this composition as a dietary bar or functional food can include flavorings, sugars, amino-sugars, proteins and/or modified starches, as well as fats and oils.

The dietary supplements, lotions or therapeutic compositions of the preferred embodiments can be formulated in any manner known by one of skill in the art. In one embodiment, the composition is formulated into a capsule or tablet using techniques available to one of skill in the art. In capsule or tablet form, the recommended daily dose for an adult human or animal would preferably be contained in one to six capsules or tablets. However, the present compositions may also be formulated in other convenient forms, such as an injectable solution or suspension, a spray solution or suspension, a lotion, gum, lozenge, food or snack item. Food, snack, gum or lozenge items can include any ingestible ingredient, including sweeteners, flavorings, oils, starches, proteins, fruits or fruit extracts, vegetables or vegetable extracts, grains, animal fats or proteins. Thus, the present compositions can be formulated into cereals, snack items such as chips, bars, gumdrops, chewable candies or slowly dissolving lozenges. The preferred embodiments contemplate treatment of all types of inflammation-based diseases, both acute and chronic. The present formulation reduces the inflammatory response and thereby promotes healing of, or prevents further damage to, the affected tissue. A pharmaceutically acceptable carrier may also be used in the present compositions and formulations.

According to the preferred embodiments, the animal may be a member selected from the group consisting of humans, non-human primates, dogs, cats, birds, horses, ruminants or other warm blooded animals. The preferred embodiments are directed primarily to the treatment of human beings. Administration can be by any method available to the skilled artisan, for example, by oral, topical, transdermal, transmucosal, or parenteral routes.

TABLE 3 below provides a list of diseases in which COX-2 enzyme expression and activity may play a role and therefore are appropriate targets for normalization or treatment by the compositions of the preferred embodiments.

TABLE 3

COX-2 Associated Diseases

| DISEASE | TISSUE |
|---|---|
| Addison's Disease | Adrenal |
| Allergies | Inflammatory cells |
| Alzheimer Disease | Nerve cells |
| Arthritis | Inflammatory cells |
| Atherosclerosis | Vessel wall |
| Colon Cancer | Intestine |
| Crohn's Disease | Intestine |
| Diabetes (type I)/type II | Pancreas |
| Eczema | Skin/Inflammatory cells |
| Graves' Disease | Thyroid |
| Guillain-Barre Syndrome | Nerve cells |
| Inflammatory Bowel Disease | Intestine |
| Leukemia | Immune cells |
| Lymphomas | Immune cells |
| Multiple Sclerosis | Nerve cells |
| Myasthenia Gravis | Neuromuscular junction |
| Osteoarthritis | Joint lining |
| Psoriasis | Skin |
| Primary Biliary Cirrhosis | Liver |
| Rheumatoid Arthritis | Joint lining |
| Solid Tumors | Various |
| Systemic Lupus Erythematosis | Multiple tissues |
| Uveitis | Eye |

The discovery of COX-2 has made possible the design of drugs that reduce inflammation without removing the protective PGs in the stomach and kidney made by COX-1. Compositions of the preferred embodiments would be useful for, but not limited to, the treatment of inflammation in a subject, and for treatment of other inflammation-associated disorders, such as, as an analgesic in the treatment of pain and headaches, or as an antipyretic for the treatment of fever. Compositions of the preferred embodiments would be useful in treating inflammation in such diseases as vascular diseases, migraine headaches, periarteritis nodosa, thyroiditis, aplastic anemia, Hodgkin's disease, sclerodma, rheumatic fever, type I diabetes, myasthenia gravis, multiple sclerosis, sacoidosis, nephrotic syndrome, Behchet's syndrome, polymyositis, gingivitis, hypersensitivity, swelling occurring after injury, myocardial ischemia and the like. Compositions of the preferred embodiments are useful as anti-inflammatory agents with the additional benefit of having significantly less harmful side effects.

The preferred embodiments can also provide a composition of matter to increase the rate at which glucosamine or chondrotin sulfate function to normalize joint movement or reduce the symptoms of osteoarthritis. For example, compositions of the preferred embodiments would be useful to treat arthritis, including but not limited to rheumatoid arthritis, spondyloathopathies, gouty arthritis, osteoarthritis, systemic lupus erythematosis, and juvenile arthritis.

Such compositions of the preferred embodiments would also be useful in the treatment of asthma, bronchitis, menstrual cramps, tendonitis, bursitis, and skin related conditions such as psoriasis, eczema, burns and dermatitis. Compositions of the preferred embodiments also would be useful to treat gastrointestinal conditions such as inflammatory bowel disease, Crohn's disease, gastritis, irritable bowel syndrome and ulcerative colitis and for the prevention or treatment of cancer such as colorectal cancer.

The compositions of the preferred embodiments would also be useful in the treatment of ophthalmic diseases, such as retinopathies, conjunctivitis, uveitis, ocular photophobia, and of acute injury to the eye tissue. The compounds would also be useful in the treatment of pulmonary inflammation, such as that associated with viral infections and cystic fibrosis. The compounds would also be useful for the treatment of certain nervous system disorders such as cortical dementias including Alzheimer's disease. As inhibitors of COX-2 mediated biosynthesis of PGE2, these compositions would also be useful in the treatment of allergic rhinitis, respiratory distress syndrome, endotoxin shock syndrome, atherosclerosis, and central nervous system damage resulting from stroke, ischemia and trauma.

The following examples are intended to illustrate but not in any way limit the preferred embodiments:

EXAMPLE 1

Synergistic Inhibition of Prostaglandin E2 Production in Murine B Cells by Curcuminoids and an Extract of Hops This example illustrates the superior COX-2 inhibitory potency and selectivity of the combination of curcuminoids and hops extract of the preferred embodiments compared to curcuminoids alone.

Inhibition of COX-2 Mediated Production of PGE2 in RAW 264.7 Cells

Equipment—balancer, analytical, Ohaus Explorer (Ohaus Model #EO1140, Switzerland), biosafety cabinet (Forma Model #F1214, Marietta, Ohio), pipettor, 100 to 1000 µL (VWR Catalog #4000-208, Rochester, NY), cell hand tally counter (VWR Catalog #23609-102, Rochester, N.Y.), $CO_2$ incubator (Forma Model #F3210, Marietta, Ohio), hemacytometer (Hausser Model #1492, Horsham, Pa.), microscope, inverted (Leica Model #DM IL, Wetzlar, Germany), multi-channel pipettor, 12-Channel (VWR Catalog #53501-662, Rochester, N.Y.), Pipet Aid (VWR Catalog #53498-103, Rochester, N.Y.), Pipettor, 0.5 to 10 µL (VWR Catalog #4000-200, Rochester, N.Y.), pipettor, 100 to 1000 µL (VWR Catalog #4000-208, Rochester, N.Y.), pipettor, 2 to 20 µL (VWR Catalog #4000-202, Rochester, N.Y.), pipettor, 20 to 200 µL (VWR Catalog #4000-204, Rochester, N.Y.), PURELAB Plus Water Polishing System (U.S. Filter, Lowell, Mass.), refrigerator, 4° C. (Forma Model #F3775, Marietta, Ohio), vortex mixer (VWR Catalog #33994-306, Rochester, N.Y.), water bath (Shel Lab Model #1203, Cornelius, Oreg.).

Cells, Chemicals, Reagents and Buffers—Cell scrapers (Corning Catalog #3008, Corning, N.Y.), dimethylsulfoxide (DMSO) (VWR Catalog #5507, Rochester, N.Y.), Dulbecco's Modification of Eagle's Medium (DMEM) (Mediatech Catalog #10-013-CV, Herndon, Va.), fetal bovine serum, heat inactivated (FBS-HI) (Mediatech Catalog #35-011-CV, Herndon, Va.), lipopolysaccharide (LPS)(Sigma Catalog #L-2654, St. Louis, Mo.), microfuge tubes, 1.7 mL (VWR Catalog #20172-698, Rochester, N.Y.), penicillin/streptomycin (Mediatech Catalog #30-001-CI, Herndon, Va.), pipet tips for 0.5 to 10 µL pipettor (VWR Catolog #53509-138, Rochester, N.Y.), pipet tips for 100-1000 µL pipettor (VWR Catolog #53512-294, Rochester, N.Y.), pipet tips for 2-20 µL and 20-200 µL pipettors (VWR Catolog #53512-260, Rochester, N.Y.), pipets, 10 mL (Becton Dickinson Catalog #7551, Marietta, Ohio), pipets, 2 mL (Becton Dickinson Catalog

7507, Marietta, Ohio, pipets, 5 mL (Becton Dickinson Catalog #7543, Marietta, Ohio), RAW 264.7 Cells (American Type Culture Collection Catalog #TIB-71, Manassas, Va.), test compounds (liquid $CO_2$ hops extract from Hopunion, Yakima, Wash.), (curcumin from Sigma (St. Louis, Mo.) (Product C 1386), 65-70% *Curcuma longa* powder), tissue culture plates, 96-well (Becton Dickinson Catalog #3075, Franklin Lanes, N.J.), Ultra-pure water (Resistance=18 megaOhm-cm deionized water).

General Procedure—RAW 264.7 cells, obtained from ATCC, were grown in DMEM medium and maintained in log phase growth. The DMEM growth medium was made as follows: 50 mL of heat inactivated FBS and 5 mL of penicillin/streptomycin were added to a 500 mL bottle of DMEM and stored at 4° C. This was warmed to 37° C. in a water bath before use and for best results should be used within three months On day one of the experiment, the log phase 264.7 cells were plated at $8 \times 10^4$ cells per well in 0.2 mL growth medium per well in a 96-well tissue culture plate. After 6 to 8 hours post plating, 100 µL of growth medium from each well was removed and replaced with 100 µL fresh medium. A 1.0 mg/mL solution of LPS, which was used to induce the expression of COX-2 in the RAW 264.7 cells, was prepared by dissolving 1.0 mg of LPS in 1 mL DMSO. It was mixed until dissolved and stored at 4° C. Immediately before use, it was thawed at room temperature or in a 37° C. water bath.

On day two of the experiment, the test materials were prepared as 1000× stock in DMSO. For example, if the final concentration of the test material was to be 10 µg/mL, a 10 mg/mL stock was prepared by dissolving 10 mg of the test material in 1 mL of DMSO. Fresh test materials were prepared on day 2 of the experiment. In 1.7 mL microfuge tubes, 1 mL DMEM without FBS was added to obtain test concentrations of 0.05, 0.10, 0.5, and 1.0 µg/mL. 2 µL of the 1000× DMSO stock of the test material was added to the 1 mL of medium without FBS. The tube contained the final concentration of the test material was concentrated 2-fold. The tube was placed in incubator for 10 minutes to equilibrate.

One-hundred mL of medium was removed from each well of the cell plates prepared on day one. One-hundred mL of equilibrated 2× final concentration the test compounds were added to cells and incubated for 90 minutes. LPS in DMEM without FBS was prepared by adding 44 µL of the 1 mg/mL DMSO stock to 10 mL of medium. For each well of cells to be stimulated, 20 µL of LPS (final concentration of LPS is 0.4 µg/mL of LPS) was added. The LPS stimulation was continued for 24 hours, after which the supernatant medium from each well was transferred to a clean microfuge tube for determination of the PGE2 content in the medium.

Determination of COX-1 Enzyme Inhibition by Curcuminoids and Hops Extract

The ability of a test material to inhibit COX-1 synthesis of PGE2 was determined essentially as described by Noreen, Y., et al. (J. Nat. Prod. 61, 2-7, 1998).

Equipment—balancer (2400 g, Acculab VI-2400, VWR Catalog #11237-300, Rochester, N.Y.), balancer, analytical, Ohaus Explorer (Ohaus Model #EO1140, Switzerland), biosafety cabinet (Forma Model #F1214, Marietta, Ohio), Freezer, −30° C. (Forma Model #F3797), Freezer, −80° C. Ultralow (Forma Model #F8516, Marietta, Ohio), heated stirring plate (VWR Catalog #33918-262, Rochester, N.Y.), ice maker (Scotsman Model #AFE400A-1A, Fairfax, S.C.), multichannel pipettor, 12-Channel (VWR Catalog #53501-662, Rochester, N.Y.), Multichannel Pipettor, 8-Channel (VWR Catalog #53501-660, Rochester, N.Y.), orbital shaker platform (Scienceware #F37041-0000, Pequannock, N.J.), pH meter (VWR Catalog #33221-010, Rochester, N.Y.), pipet aid (VWR Catalog #53498-103, Rochester, N.Y.), pipettor, 0.5 to 10 µL (VWR Catalog #4000-200, Rochester, N.Y.), pipettor, 100 to 1000 µL (VWR Catalog #4000-208, Rochester, N.Y.), pipettor, 2 to 20 µL (VWR Catalog #4000-202, Rochester, N.Y.), pipettor, 20 to 200 µL (VWR Catalog #4000-204, Rochester, N.Y.), PURELAB Plus Water Polishing System (U.S. Filter, Lowell, Mass.), refrigerator, 4° C. (Forma Model #F3775, Marietta, Ohio), vacuum chamber (Sigma Catalog #Z35, 407-4, St. Louis, Mo.), vortex mixer (VWR Catalog #33994-306, Rochester, N.Y.)

Supplies and Reagents—96-Well, round-bottom plate (Nalge Nunc #267245, Rochester, N.Y.), arachidonic acid (Sigma Catalog #A-3925, St. Louis, Mo.), centrifuge tubes, 15 mL, conical, sterile (VWR Catalog #20171-008, Rochester, N.Y.), COX-1 enzyme (ovine) 40,000 units/mg (Cayman Chemical Catalog #60100, Ann Arbor, Mich.), dimethylsulfoxide (DMSO) (VWR Catalog #5507, Rochester, N.Y.), ethanol 100% (VWR Catalog #MK701908, Rochester, N.Y.), epinephrine (Sigma Catalog #E-4250, St. Louis, Mo.), glutathione (reduced) (Sigma Catalog # G-6529, St. Louis, Mo.), graduated cylinder, 1000 mL (VWR Catalog #24711-364, Rochester, N.Y.), hematin (porcine) (Sigma catalog # H-3281, St. Louis, Mo.), hydrochloric acid (HCl) (VWR Catalog #VW3110-3, Rochester, N.Y.), KimWipes (Kimberly Clark Catalog #34256, Roswell, Ga.), microfuge tubes, 1.7 mL (VWR Catalog #20172-698, Rochester, N.Y.), NaOH (Sigma Catalog #S-5881, St. Louis, Mo.), pipet tips for 0.5 to 10 µL pipettor (VWR Catolog #53509-138, Rochester, N.Y.), pipet tips for 100-1000 µL pipettor (VWR Catolog #53512-294, Rochester, N.Y.), pipet tips for 2-20 µL and 20-200 µL pipettors (VWR Catolog #53512-260, Rochester, N.Y.), prostaglandin E2 (Sigma Catalog # P-5640, St. Louis, Mo.), prostaglandin F2alpha (Sigma Catalog # P-0424, St. Louis, Mo.), stir bar, magnetic (VWR Catalog #58948-193, Rochester, N.Y.), storage bottle, 1000 mL (Corning Catalog #1395-IL, Corning, N.Y.), storage bottle, 100 mL (Corning Catalog #1395-100, Corning, N.Y.), $CO_2$ extract of hops (Hopunion, Yakima, Wash.), curcumin (Sigma, St. Louis, Mo., (Product C 1386), 65-70% *Curcuma longa* powder), Tris-HCl (Sigma Catalog #T-5941, St. Louis, Mo.), ultra-pure water (Resistance=18 megaohm-cm deionized water).

General Procedure—Oxygen-free 1.0M Tris-HCl buffer (pH 8.0) was prepared as follows. In a 1000 mL beaker, 12.11 g Trizma HCl was dissolved into 900 mL ultra-pure water. The beaker was placed on a stir plate with a stir bar. NaOH was added until the pH reached 8.0. The volume was adjusted to a final volume of 1000 mL and stored in a 1000 mL storage bottle.

The Tris-HCl buffer was placed into a vacuum chamber with the top loosened and the air pump was turned on until the buffer stopped bubbling. The vacuum chamber was then turned off and the storage bottle was tightly covered. This step was repeated each time when oxygen-free Tris-HCl buffer was used.

One mL cofactor solution was prepared by adding 1.3 mg (−) epinephrine, 0.3 mg reduced glutathione and 1.3 mg hematin to 1 mL oxygen free Tris-HCl buffer. The solutions of the test material were prepared as needed. i.e. 10 mg of aspirin was weighed and dissolved into 1 mL DMSO.

Enzymes, i.e. prostaglandin E2 or prostaglandin F2alpha, were dissolved in oxygen free Tris-HCl buffer as follows, i.e. on ice, 6.5 µL of enzyme at 40,000 units/mL was taken and added to 643.5 µL of oxygen free Tris-HCl buffer. This enzyme solution is enough for 60 reactions. The COX-1 enzyme solution was prepared as follows: In a 15 mL centrifuge tube, 10 µL COX-1 enzyme at 40,000 units/mL was added to oxygen free Tris-HCl with 50 µL of the cofactor solution per reaction. The mixture was incubated on ice for 5 minutes. For 60 reactions, 650 µL enzyme were added in oxygen free Tris-HCl buffer with 3.25 mL cofactor solution.

Sixty microliters of the enzyme solution were combined with 20 µL of the test solution in each well of a 96 well plate. Final concentrations of the test solutions were 100, 50, 25, 12.5, 6.25 and 3.12 µg/mL. The plates were preincubated on ice for 10 minutes. Twenty µL arachidonic acid (30 µM) was added and incubated for 15 minutes at 37° C.

Two M HCl was prepared by diluting 12.1 N HCl in a 100 mL storage bottle. 83.5 mL ultra-pure water was added and then 16.5 mL 12.1 N HCl was added. It was stored in a 100 mL storage bottle and placed in the Biosafty cabinet. The reaction was terminated by adding 10 µL 2 M HCl. The final solution was used as the supernatant for the $PGE_2$ assay.

Determination of PGE2 Concentration in Medium

The procedure followed was that essentially described by Hamberg, M. and Samuelsson, B. (*J. Biol. Chem.* 1971. 246, 6713-6721); however a commercial, nonradioactive procedure was employed.

Equipment—freezer, −30° C. (Forma Model #F3797), heated stirring plate (VWR Catalog #33918-262, Rochester, N.Y.), multichannel pipettor, 12-Channel (VWR Catalog #53501-662, Rochester, N.Y.), orbital shaker platform (Scienceware #F37041-0000, Pequannock, N.J.), Pipet Aid (VWR Catalog #53498-103, Rochester, N.Y.), pipettor, 0.5 to 10 µL (VWR Catalog #4000-200, Rochester, N.Y.), pipettor, 100 to 1000 µL (VWR Catalog #4000-208, Rochester, N.Y.), pipettor, 2 to 20 µL (VWR Catalog #4000-202, Rochester, N.Y.), pipettor, 20 to 200 µL (VWR Catalog #4000-204, Rochester, N.Y.), plate reader (Bio-tek Instruments Model #Elx800, Winooski, Vt.), PURELAB Plus Water Polishing System (U.S. Filter, Lowell, Mass.), refrigerator, 4° C. (Forma Model #F3775, Marietta, Ohio).

Chemicals, Reagents and Buffers—Prostaglandin $E_2$ EIA Kit-Monoclonal 480-well (Cayman Chemical Catalog # 514010, Ann Arbor, Mich.), centrifuge tube, 50 mL, conical, sterile (VWR Catalog #20171-178, Rochester, N.Y.), Dulbecco's Modification of Eagle's Medium (DMEM) (Mediatech Catalog #10-013-CV, Herndon, Va.), graduated cylinder, 100 mL (VWR Catalog #24711-310, Rochester, N.Y.), KimWipes (Kimberly Clark Catalog #34256, Roswell, Ga.), microfuge tubes, 1.7 mL (VWR Catalog #20172-698, Rochester, N.Y.), penicillin/streptomycin (Mediatech Catalog #30-001-CI, Herndon, Va.), pipet tips for 0.5 to 10 µL pipettor (VWR Catolog #53509-138, Rochester, N.Y.), pipet tips for 100-1000 µL pipettor (VWR Catolog #53512-294, Rochester, N.Y.), pipet tips for 2-20 µL and 20-200 µL pipettors (VWR Catolog #53512-260, Rochester, N.Y.), pipets, 25 mL (Becton Dickinson Catalog #7551, Marietta, Ohio), storage bottle, 100 mL (Corning Catalog #1395-100, Corning, N.Y.), storage bottle, 1000 mL (Corning Catalog #1395-IL, Corning, N.Y.), ultra-pure water (Resistance=18 megaohm-cm deionized water).

General Procedure—EIA Buffer was prepared by diluting the contents of the EIA Buffer Concentrate (vial #4) with 90 ml of Ultra-pure water. Vial #4 was rinsed several times to ensure all crystals had been removed and was then placed into a 100 mL storage bottle and stored at 4° C.

The Wash Buffer was prepared by diluting Wash Buffer Concentrate (vial #5) 1:400 with Ultra-pure water. 0.5 ml/liter of Tween 20 (vial #5a) was then added (using a syringe for accurate measurement). To prepare one liter of Wash Buffer add 2.5 ml Wash Buffer Concentrate, 0.5 ml Tween-20, and 997 ml Ultra-pure water. The solution was stored in a 1 liter storage bottle at 4° C.

The Prostaglandin $E_2$ standard was reconstituted as follows. A 200 µL pipet tip was equilibrated by repeatedly filling and expelling the tip several times in ethanol. The tip was used to transfer 100 µL of the $PGE_2$ Standard (vial #3) into a 1.7 mL microfuge tube. 900 µl Ultra-pure water was added to the tube and stored at 4° C., which was stable for ~6 weeks. The Prostaglandin $E_2$ acetylcholinesterase tracer was reconstituted as follows. 100 µL $PGE_2$ tracer (vial #2) was mixed with 30 mL of the EIA Buffer in a 50 mL centrifuge tube and stored at 4° C.

The Prostaglandin $E_2$ monoclonal antibody was reconstituted as follows. 100 µL $PGE_2$ Antibody (vial #1) was mixed with 30 mL of the EIA buffer in a 50 mL centrifuge tube and stored at 4° C.

DMEM with penicillin/streptomycin was prepared by adding 5 mL penicillin/streptomycin into 500 mL DMEM and stored at 4° C.

The plates were set up as follows: Each plate contained a minimum of two blanks (B), two non-specific binding wells (NSB), two maximum binding wells ($B_0$), and an eight point standard curve run in duplicate (S1-S8). Each sample was assayed at a minimum of two dilutions and each dilution was run in duplicate.

The standard was prepared as follows: Eight 1.7 mL microuge tubes were labeled as tubes 1-8. 900 µL DMEM into was added to tube 1 and 500 µL DMEM to tubes 2-8. 100 µL of the $PGE_2$ standard was added to tube 1 and mixed. Five-hundred mL of solution was taken from tube 1 and put into tube 2, and this process was repeated through tube 8.

Fifty mL EIA Buffer and 50 µl DMEM were added into the NSB wells. Fifty µl DMEM was added to the $B_0$ wells. Fifty mL of solution was taken from tube #8 and added to both the lowest standard wells (S8). Fifty mL was taken from tube #7 and added to each of the next two wells. This was continued through to tube #1. (the same pipet tip was used for all 8 of the standards making sure to equilibrate the tip in each new standard by pipeting up and down in that standard. Using a P200, 50 µl of each sample at each dilution was added to the sample wells.

Using a12 channel pipetor, 50 µl of the Prostaglandin $E_2$ acetylcholinesterase tracer was added to each well except the Total Activity (TA) and the Blank (B) wells. Using the 12 channel pipetor, 50 µl of the Prostaglandin $E_2$ monoclonal antibody was added to each well except the Total Activity (TA), the (NSB), and the Blank (B) wells. The plate was covered with plastic film (item #7) and incubated for 18 hours at 4° C.

The plates were developed as follows: one 100 µL vial of Ellman's Reagent (vial #8) was reconstituted with 50 ml of Ultra-pure water in a 50 mL centrifuge tube. It was protected from light and used the same day. The wells were washed and rinsed five times with Wash Buffer using a 12 channel pipettor. Two-hundred mL of Ellman's Reagent was added to each well using a 12 channel pipettor and 5 µl of Tracer to the total activity (TA) wells was then added to each well using a P10 pipette. The plate was covered with a plastic film and placed on orbital shaker in the dark for 60-90 minutes.

The plate was read in the Bio-tek plate reader at a single wavelength between 405 and 420 nm. Before reading each plate, the bottom was wiped with a Kim wipe. The plate should be read when the absorbance of the wells is in the range of 0.3-0.8 A.U. If the absorbance of the wells exceeded 1.5, they were washed and fresh Ellmans' Reagent was added and then redeveloped.

Calculation of Synergy and Combination Index

Synergy between the curcuminoids and andrographolide was assessed using CalcuSyn (BIOSOFT, biosoft.com). This statistical package performs multiple drug dose-effect calculations using the Median Effect methods described by T-C Chou and P. Talaly (Trends Pharmacol. Sci. 4:450-454), hereby incorporated by reference.

Briefly, it correlates the "Dose" and the "Effect" in the simplest possible form: fa/fu=(C/Cm)m, where C is the concentration or dose of the compound and Cm is the median-effective dose signifying the potency. Cm is determined from the x-intercept of the median-effect plot. The fraction affected by the concentration of the test material is fa and the fraction unaffected by the concentration is fu (fu=1−fa). The exponent m is the parameter signifying the sigmoidicity or shape of the dose-effect curve. It is estimated by the slope of the median-effect plot.

The median-effect plot is a plot of x=log(C) vs y=log(fa/fu) and is based on the logarithmic form of Chou's median-effect equation. The goodness of fit for the data to the median-effect equation is represented by the linear correlation coefficient r of the median-effect plot. Usually, the experimental data from enzyme or receptor systems have an r>0.96, from tissue culture an r>0.90 and from animal systems an r>0.85.

Synergy of test components is quantified using the combination index (CI) parameter. The CI of Chou-Talaly is based on the multiple drug-effect and is derived from enzyme kinetic models (Chou, T.-C. and Talalay, P. (1977) A simple generalized equation for the analysis of multiple inhibitions of Michaelis-Menten kinetic systems. J. Biol. Chem. 252: 6438-6442). The equation determines only the additive effect rather than synergism or antagonism. However, we define synergism as a more than expected additive effect, and antagonism as a less than expected additive effect as proposed by Cho and Talalay in 1983 (Trends Pharmacol. Sci. (1983) 4:450-454). Using the designation of CI=1 as the additive effect, we obtain for mutually exclusive compounds that have the same mode of action or for mutually non-exclusive drugs that have totally independent modes of action the following relationships: CI<1,=1, and >1 indicating synergism, additivity and antagonism, respectively.

Expected median inhibitory concentrations of the two-component combinations were estimated using the relationship:

$$[1/\text{Expected } IC_{50}] = [A/IC_{50}A] + [B/IC_{50}B]$$

where A=mole fraction of component A in the combination and B=the mole fraction of component B in the combination.

TABLE 4 illustrates the observed and expected median inhibitory concentrations for curcumin and hops extract for PGE2 production by COX-2 in the RAW 264.7 cell assay. While the expected $IC_{50}$ for the 10:1 combination of curcumin and hops extract was 1.6 μg/mL, the observed value was 0.77 μg/mL or 2-fold greater. This level of difference was unexpected and constitutes a novel finding for the combined COX-2 inhibitory activity of the 1:10 combination of curcumin and hops extract.

TABLE 4

Observed and Expected Median Inhibitory Concentrations for a (10:1) Formulation of Curcumin and Hops Extract

| Composition | Ratio | $IC_{50}$ (μg/ml) |
|---|---|---|
| Hops Extract | | 0.216 |
| Curcumin | | 4.5 |
| Combined | | |
| Hops Extract Contribution | 1 | 0.071 |
| Curcumin Contribution | 10 | 0.715 |
| Observed | | 0.786 |
| Calculated | | 1.605 |

Statistical analysis of inhibition of COX-2 production of PGE2 in the RAW 264.7 cell model for the 1:10 combination of curcumin and hops extract is presented in TABLE 5. The CI for this combination was 0.490, 0.472 and 0.454, respectively, for the $IC_{50}$, $IC_{75}$ and $IC_{90}$. These CI values indicate strong synergy between curcumin and hops extract over the complete dose-response curve.

TABLE 5

Combination Index for a 1:10 Formulation of Curcumin and Hops Extract

| Combination Index | | | |
|---|---|---|---|
| $IC_{50}$ | $IC_{75}$ | $IC_{90}$ | Mean CI |
| 0.490 | 0.472 | 0.454 | 0.472 |

The medium inhibitory concentration of COX-2 by curcumin alone in the RAW 264.7 cell model was 4.01 μg/mL (TABLE 6). Inhibition of COX-1 enzyme activity by curcumin was somewhat higher with an $IC_{50}$ of 10.0 μg/mL. Hops extract exhibited an $IC_{50}$ of PGE2 inhibition by COX-2 of 0.21 μg/mL and an $IC_{50}$ for COX-1 enzyme inhibition estimated at 6.25 μg/mL; the COX-2 specificity of curcumin alone was 2.5 and for hops extract, it was 29.5. Eleven formulations of curcumin and hops extract exhibited COX-2 specificity ranging from 48.6 to 11.2, with a median COX-2 specificity of 17.4. All of the combinations of curcumin and hops extract unexpectedly demonstrated COX-2 specificity greater than the nominal 5.0 suggested as the minimum for pharmaceutical products designed to limit PGE2 production specifically through inhibition of COX-2. This finding indicates that combinations of curcumin and a hops extract could function as potent anti-inflammatory formulations without the GI side effects seen with COX-1 inhibition.

TABLE 6

COX-2 Specificity for Curcumin, Hops Extract and Eleven Formulations of Curcumin and Hops Extract

| Hops Extract:Curcumin [x:y] | Hops Extract [%] | Curcumin [%] | COX-1 $IC_{50}$ [μg/ml] | COX-2 $IC_{50}$ [μg/ml] | COX-1/ COX-2 |
|---|---|---|---|---|---|
|  | 100 | 0 | 6.25 | 0.212 | 29.5 |
| [10:1] | 91 | 9 | 6.471 | 0.186 | 34.8 |
| [8:1] | 89 | 11 | 6.522 | 0.426 | 15.3 |
| [6:1] | 86 | 14 | 6.604 | 0.590 | 11.2 |
| [4:1] | 80 | 20 | 6.757 | 0.389 | 17.4 |
| [2:1] | 67 | 33 | 7.143 | 0.147 | 48.6 |
| [1:1] | 50 | 50 | 7.692 | 0.452 | 17.0 |
| [1:2] | 33 | 67 | 8.333 | 0.332 | 25.1 |
| [1:4] | 20 | 80 | 8.929 | 0.377 | 23.7 |
| [1:6] | 14 | 86 | 9.211 | 0.449 | 20.5 |
| [1:8] | 11 | 89 | 9.375 | 0.563 | 16.7 |
| [1:10] | 9 | 91 | 9.483 | 0.786 | 12.1 |
|  | 0 | 100 | 10.0 | 4.01 | 2.5 |

EXAMPLE 2

Normalization of Joint Functioning Following Trauma

A representative composition of the present invention as a dietary supplement would be in an oral formulation, i.e. tablets, that would supply one of the following combinations: (a) 15 mg curcuminoid/kg per day and 6.0 mg humulone/kg per day; (b) 15 mg curcuminoid/kg per day and 6.0 mg upulons/kg per day; (c) 15 mg curcuminoid/kg per day and 6.0 mg dihydroisohumulones/kg per day. Normalization of joint movement following physical trauma due to exercise or repetitive movement stress would be expected to occur following two to ten doses. This result would be expected in all animals.

EXAMPLE 3

Clinical Effectiveness of Lotion Formulations in the Treatment of Acne Rosacea

A lotion designed to contain one of the following: (a) 0.1% wt curcuminoids and 0.5% humulone; or (b) 0.1% wt curcuminoids and 0.5% lumulone is applied to affected areas of patients who have exhibited acne rosace as diagnosed by their health practitioner and confirmed by an independent board-certified dermatologist. Self-evaluation tests and are administered one week prior to the study to quantify the surface area affected and redness. In addition, similar variables are scored by the professional clinical staff not aware of the patients treatment status. These evaluations are repeated on Days 0, 7, 14 and 21.

Patients are randomly assigned to the test formulation or placebo at the start of the study. The test formulation and placebo are applied to the affected area one or two times per day. Treatment for health conditions such as diabetes, hypertension, etc. is allowed during the study. Scores are statistically compared between the test formulation and the placebo for each of the four observational periods. Patients treated with the composition of the present invention in a lotion formulation are considered improved if the patients' scores improve by greater than 20% from the pre-test scores within each category evaluated. The percentage of persons exhibiting improvement is compared between the combination formulations and the placebo control. The difference between the two groups is considered statistically significant if the probability of rejecting the null hypothesis when true is less than five percent.

EXAMPLE 4

Clinical Effectiveness of Lotion Formulation in the Treatment of Psoriasis

This example is performed in the same manner as described in Example 3, except that the composition is applied to affected areas of patients who have exhibited psoriasis as diagnosed by their own practitioner and confirmed by an independent board-certified dermatologist. Self-evaluation tests are administered one week prior to the study to quantify the surface area affected and skin condition. In addition, similar variables are scored by the professional clinical staff not aware of the patients treatment status. These evaluations are repeated on Days 0, 7, 30 and 60.

Patients are randomly assigned to the test formulation or placebo at the start of the study. The test formulation and placebo are applied to the affected area one or two times per day. Treatment for health conditions such as diabetes, hypertension, etc. is allowed during the study. Scores are statistically compared between the test formulation and the placebo for each of the four observational periods. Patients treated with the composition of the present invention as the test lotion formulation are considered improved if the patients' scores improve by greater than 20% from the pre-test scores within each category evaluated. The percentage of persons exhibiting improvement is compared between the test formulation and the placebo control. The difference between the two groups is considered statistically significant if the probability of rejecting the null hypothesis when true is less than five percent.

EXAMPLE 5

Clinical Effectiveness of a Formulation in the Treatment of Alzheimer's Disease

An oral formulation as described in Example 2 is administered to patients who have manifested an early stage of Alzheimer's Disease (AD), as diagnosed by their practitioner and confirmed by an independent board-certified neurologist. Two weeks before the clinical trial, the patients undergo appropriate psychoneurological tests such as the Mini Mental Status Exam (MMSE), the Alzheimer Disease Assessment Scale (ADAS), the Boston Naming Test (BNT), and the Token Test (TT). Neuropsychological tests are repeated on Day 0, 6 weeks and 3 months of the clinical trial. The tests are performed by neuropsychologists who are not aware of the patient's treatment regimen.

Patients are randomly assigned to the test formulation or placebo at the start of the study. The test formulation and placebo are taken orally one or two times per day. Treatment for conditions such as diabetes, hypertension, etc. is allowed during the study. Scores are statistically compared between the test formulation and the placebo for each of the three observational periods. Without treatment, the natural course of AD is significant deterioration in the test scores during the course of the clinical trial. Patients treated with the composition of the present invention as the test formulation are considered improved if the patients' scores remain the same or improve during the course of the clinical trial.

EXAMPLE 6

Oral Formulation in the Treatment and Prevention of Colon Cancer

An oral formulation as described in Example 2 is administered to patients who have manifested an early stage of colon cancer as diagnosed by their own practitioner and confirmed by a independent board-certified oncologist.

Patients are randomly assigned to the test formulation or a placebo at the start of the study. The test formulation and placebo are taken orally one or two times per day. Treatment for conditions such as diabetes, hypertension, etc. is allowed during the study. Endoscopic evaluations are made at one, two, six and twelve months. Evidence of reappearance of the tumor during any one of the four follow-up clinical visits is considered a treatment failure. The percentage of treatment failures is compared between the test formulation and the placebo control. Under the experimental conditions described, the test material is expected to decrease the tumor incidence with respect to the control group. The difference between the two groups is considered statistically significant if the probability of rejecting the null hypothesis when true is less than five percent.

EXAMPLE 7

Oral Formulation for the Treatment of Irritable Bowel Syndrome

An oral formulation as described in Example 2 is administered to patients who have manifested irritable bowel syndrome as diagnosed by their practitioner. Normal bowel functioning is restored within 24 hours.

EXAMPLE 8

Normalization of Joint Functioning in Osteoarthritis

Using compositions described in Example 2 normalization of joint stiffness due to osteoarthritis occurs following five to twenty doses, in the presence or absence of glucosamine or chondroitin sulfate. In addition, the composition does not interfere with the normal joint rebuilding effects of these two proteoglycan constituents, unlike traditional non-steroidal anti-inflammatory agents.

In summary, a certain embodiment is a composition for inhibition of inducible COX-2 activity and having minimal effect on COX-1 activity, said composition comprising, as a first component an effective amount of a curcuminoid species and an effective amount of a second component selected from the group consisting of an alpha-acid species and a beta-acid species or derivatives thereof. The curcuminoid species is preferably curcumin, demethoxycurcurmin, or bis-demethoxycurcumin. The alpha-acid species is preferably humulone, cohumulone, isohumulone, isoprehumulone, hulupone, adhumulone, xanthohumol A, or xanthohumol B. The beta-acid species is preferably lupulone, colupulone, adlupulone, tetrahydroisohumulone, hexahydrocolupulone or dihydro-isohumulone. The first or the second components of the present composition may be of pharmaceutical grade or derived from plant(s) or plant extract(s). The first or second components may also be conjugated with a compounds such as mono- or di-saccharides, amino acids, sulfates, succinates, acetates or glutathione. The compositions of the preferred embodiments can be formulated in a pharmaceutically acceptable carrier and contain additives, such as antioxidants, vitamins, minerals, proteins, fats, carbohydrates, glucosamine, chondrotin sulfate or aminosugars.

Other embodiments include methods of dietary supplementation of the compositions of the preferred embodiments to reduce the symptoms in animals suffering from symptoms of inflammation. The composition is formulated in a dosage form such that said administration provides from about 0.001 to about 30.0 mg body weight per day of each curcuminoid species, and from about 0.5 to about 20.0 mg/kg bodyweight per day of alpha-acid species or beta-acid species. The composition is administered in an amount sufficient to maintain a serum concentration of about 0.1 to about 50 μM of each curcuminoid species, and from about 0.001 to about 50 μM of each alpha-acid species or beta-acid species. The animal may be humans, non-human primates, dogs, cats, birds, reptiles, amphibians, horses or ruminants. The administration may be an oral, parenteral, topical, transdermal or transmucosal delivery system.

Thus, among the various formulations taught there has been disclosed a formulation comprising curcuminoids, as the first component, and a second compound selected from the group consisting of alpha-acids and beta-acids. These combinations can provide for a synergistic anti-inflammatory effect in response to physical or chemical injury or abnormal immune stimulation due to a biological agent or unknown etiology. It will be readily apparent to those skilled in the art that various changes and modifications of an obvious nature may be made without departing from the spirit of the invention, and all such changes and modifications are considered to fall within the scope of the invention as defined by the appended claims.

What is claimed is:

1. A method of treating diabetes, comprising administering to an individual having diabetes a composition comprising a curcuminoid and a component selected from the group consisting of tetrahydroisohumulone and dihydro-isohumulone.

2. The method of claim 1, wherein said curcuminoid is selected from the group consisting of curcumin, demethoxycurcumin, and bisdemethoxycurcumin.

3. The method of claim 1, wherein said composition is formulated in a pharmaceutically acceptable carrier.

4. The method of claim 1, wherein said composition further comprises one or more members selected from the group consisting of antioxidants, vitamins and minerals.

5. The method of claim 1, wherein said composition further comprises one or more members selected from the group consisting of proteins, fats, carbohydrates, glucosamine, chondrotin sulfate and aminosugars.

6. The method of claim 1, wherein said curcuminiod or said component is conjugated with monosaccharides, disaccharides, amino acids, sulfates, succinates, acetates or glutathione.

* * * * *